(12) United States Patent
Gerrans et al.

(10) Patent No.: US 9,180,281 B2
(45) Date of Patent: Nov. 10, 2015

(54) ADJUSTABLE BALLOON CATHETER FOR EXTRAVASATED DRUG DELIVERY

(75) Inventors: Lawrence J. Gerrans, San Anselmo, CA (US); Erhan H. Gunday, Great Neck, NY (US)

(73) Assignee: Sanovas, Inc., San Rafael, CA (US)

( * ) Notice: Subject to any disclaimer, the term of this patent is extended or adjusted under 35 U.S.C. 154(b) by 705 days.

(21) Appl. No.: 13/436,358

(22) Filed: Mar. 30, 2012

(65) Prior Publication Data

US 2012/0259215 A1     Oct. 11, 2012

Related U.S. Application Data

(60) Provisional application No. 61/473,460, filed on Apr. 8, 2011.

(51) Int. Cl.
*A61M 31/00*     (2006.01)
*A61M 25/10*     (2013.01)
*A61M 25/00*     (2006.01)

(52) U.S. Cl.
CPC ......... *A61M 25/1011* (2013.01); *A61M 25/007* (2013.01); *A61M 25/1018* (2013.01); *A61M 2025/105* (2013.01); *A61M 2025/109* (2013.01); *A61M 2025/1015* (2013.01); *A61M 2025/1052* (2013.01)

(58) Field of Classification Search
CPC ............... A61M 2025/105; A61M 2025/1052; A61M 2025/1015; A61M 25/1011; A61B 17/12045; A61B 2017/12127; A61B 2017/22054
See application file for complete search history.

(56) References Cited

U.S. PATENT DOCUMENTS

| | | | |
|---|---|---|---|
| 4,186,745 A | 2/1980 | Lewis et al. |
| 4,824,436 A | 4/1989 | Wolinsky |
| 4,994,033 A | 2/1991 | Shockey et al. |
| 5,049,132 A | 9/1991 | Shaffer et al. |
| 5,304,121 A | 4/1994 | Sahatjian |
| 5,397,307 A | 3/1995 | Goodin |

(Continued)

FOREIGN PATENT DOCUMENTS

| | | | |
|---|---|---|---|
| DE | 19533601 A1 | 3/1996 |
| EP | 0419154 A1 | 3/1991 |

(Continued)

OTHER PUBLICATIONS

European Search Report Application No. EP 12 30 5409 Completed: Jun. 21, 2012; Mailing Date: Jul. 3, 2012 9 pages.

*Primary Examiner* — Elmer Chao
(74) *Attorney, Agent, or Firm* — St. Onge Steward Johnston & Reens LLC

(57) ABSTRACT

An adjustable balloon catheter for extravasated drug delivery is disclosed generally including an outer catheter with a first balloon and an inner catheter with a second balloon. The inner catheter is moveably disposed in a lumen of the outer catheter such that the inner catheter moves relative to the outer catheter, changing the distance between the balloons. A fluid source supplies air to the catheters via lumens therein to inflate the balloons to create a chamber between them, and at least one of the catheters has a lumen for delivering a therapeutic and/or diagnostic agent to the chamber. The inner catheter is then moved relative to the outer catheter to decrease the size of the chamber between the balloons and decrease the fluid pressure therein such that the therapeutic and/or diagnostic agent is extravasated into the surrounding tissue.

16 Claims, 5 Drawing Sheets

(56) References Cited

U.S. PATENT DOCUMENTS

| | | | |
|---|---|---|---|
| 5,611,775 A | 3/1997 | Machold et al. | |
| 5,674,192 A | 10/1997 | Sahatjian et al. | |
| 5,707,352 A | 1/1998 | Sekins et al. | |
| 5,873,852 A | 2/1999 | Vigil et al. | |
| 6,048,332 A | 4/2000 | Duffy et al. | |
| 6,129,705 A | 10/2000 | Grantz | |
| 6,485,500 B1 | 11/2002 | Kokish et al. | |
| 6,544,221 B1 | 4/2003 | Kokish et al. | |
| 6,575,932 B1 | 6/2003 | O'Brien et al. | |
| 6,623,452 B2 | 9/2003 | Chien et al. | |
| 6,685,648 B2 | 2/2004 | Flaherty et al. | |
| 6,706,013 B1 | 3/2004 | Bhat et al. | |
| 6,923,754 B2 * | 8/2005 | Lubock | 600/3 |
| 7,462,165 B2 | 12/2008 | Ding et al. | |
| 7,569,032 B2 | 8/2009 | Naimark et al. | |
| 7,611,484 B2 | 11/2009 | Wellman et al. | |
| 7,658,966 B2 | 2/2010 | Kokish | |
| 7,727,226 B2 | 6/2010 | Chang et al. | |
| 2002/0010418 A1 * | 1/2002 | Lary et al. | 604/101.04 |
| 2003/0114791 A1 | 6/2003 | Rosenthal et al. | |
| 2004/0230131 A1 | 11/2004 | Kassab et al. | |
| 2005/0227266 A1 * | 10/2005 | Ross et al. | 435/6 |
| 2005/0249667 A1 * | 11/2005 | Tuszynski et al. | 424/9.3 |
| 2006/0189930 A1 | 8/2006 | Lary et al. | |
| 2008/0208118 A1 | 8/2008 | Goldman | |
| 2009/0171268 A1 * | 7/2009 | Williams et al. | 604/26 |
| 2010/0082012 A1 | 4/2010 | Hattangadi et al. | |
| 2010/0121270 A1 | 5/2010 | Gunday et al. | |

FOREIGN PATENT DOCUMENTS

| | | |
|---|---|---|
| WO | 2008042347 A2 | 4/2008 |
| WO | 2009125380 A1 | 10/2009 |

* cited by examiner

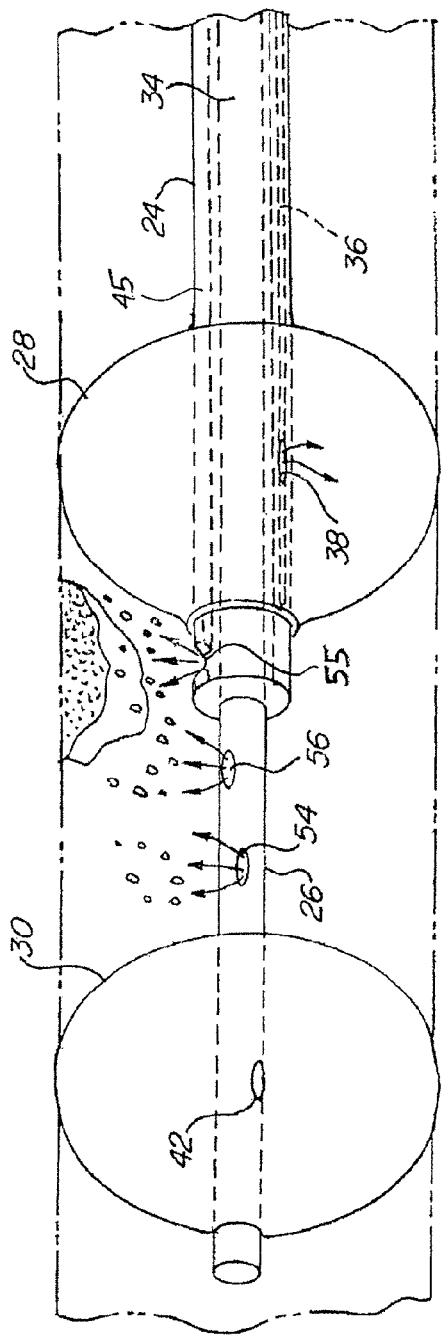
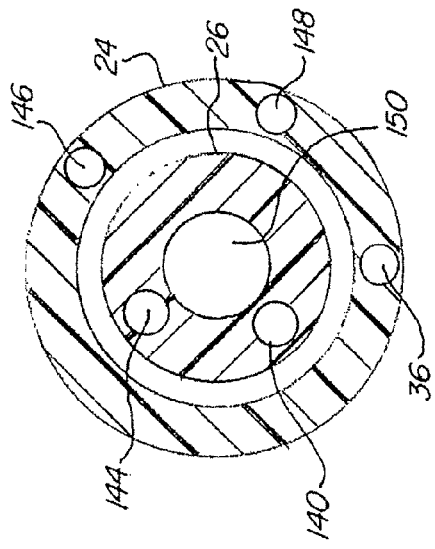
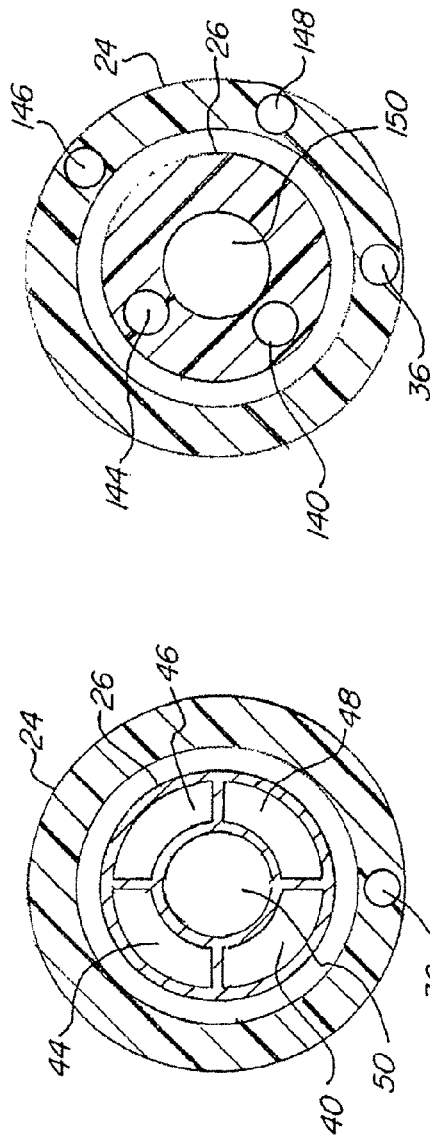

ADJUSTABLE BALLOON CATHETER FOR EXTRAVASATED DRUG DELIVERY

CROSS-REFERENCE TO RELATED APPLICATIONS

The present application claims the benefit under 35 U.S.C. §119(e) of the U.S. Provisional Patent Application Ser. No. 61/473,460 filed on Apr. 8, 2011, the content of which is incorporated by reference herein in its entirety.

FIELD OF THE INVENTION

The present invention relates to methods and systems for delivering therapeutic and/or diagnostic agents to specific locations within and adjacent to bodily cavities and tissues. More specifically, the invention relates to a method and system for localized delivery of therapeutic and/or diagnostic agents via an adjustable balloon catheter system that facilitates extravasation of the agent into cellular membranes and structural walls of bodily cavities and tissues.

BACKGROUND OF THE INVENTION

In diagnosing and treating diseases of various body cavities and organs, it is necessary to deliver diagnostic and/or therapeutic agents to the organs at specified locations. Most common routes of drug delivery include a non-invasive peroral (through the mouth), topical (skin), transmucosal (nasal, buccal/sublingual, vaginal, ocular and rectal) and inhalation routes. However, many therapeutic and diagnostic agents in general may not be delivered using these routes because they might be susceptible to enzymatic degradation or cannot be absorbed into the systemic circulation efficiently due to molecular size and charge issues, and thus, will not be therapeutically effective. For this reason, many such drugs have to be delivered by injection.

There are several known problems associated with the injection process. One of such problems is undesirable extravasation of the diagnostic or therapeutic agents into tissue, which is particularly prevalent with intravenously injected agents. Extravasation generally refers to leakage of fluids out of a container, and more specifically refers to leakage of intravenous drugs from a vein into surrounding tissues, resulting in an injury to the tissues. Once the intravenous extravasation has occurred, damage can continue for months and involve nerves, tendons and joints. If treatment is delayed, surgical debridement, skin grafting, and even amputation have been known to be the unfortunate consequences.

Occurrence of extravasation is possible with all intravenous drugs, but it is a particularly significant problem with cytoxic drugs used for treatment of cancer (i.e. during chemotherapy).

Chemotherapy is the general term for any treatment involving the use of chemical agents to stop cancer cells from growing. Chemotherapy can eliminate cancer cells at sites great distances from the original cancer. As a result, chemotherapy is considered a systemic treatment. More than half of all people diagnosed with cancer receive chemotherapy. A chemotherapy regimen (a treatment plan and schedule) usually includes drugs to fight cancer plus drugs to help support completion of the cancer treatment.

Chemotherapy can be administered through a vein, injected into a body cavity, or delivered orally in the form of a pill, depending on which drug is used. Chemotherapy works by destroying cancer cells. Unfortunately, it cannot tell the difference between a cancer cell and some healthy cells. Thus, chemotherapy often eliminates not only the fast-growing cancer cells, but also other fast-growing cells in the body, including hair and blood cells. Some cancer cells grow slowly while others grow rapidly. As a result, different types of chemotherapy drugs target the growth patterns of specific types of cancer cells.

Each chemotherapy drug works differently and is effective at a specific time in a life cycle of the cell it targets. Brachytherapy, sometimes called seed implantation, is an outpatient procedure used in the treatment of different kinds of cancer. The radioactive "seeds" are carefully placed inside of the cancerous tissue and positioned in a manner that will attack the cancer most efficiently. The radioactive seeds are about the size of a grain of rice, and give off radiation that travels only a few millimeters to kill nearby cancer cells. There are two different kinds of brachytherapy: permanent, when the seeds remain inside the body, and temporary, when the seeds are inside of the body and are then removed. With permanent implants (e.g. prostate), the radioactivity of the seeds typically decays with time.

The other type of chemotherapy is when cytotoxic agents are delivered intravenously. Veins of people receiving chemotherapy are often fragile, mobile, and difficult to cannulate. Patients who receive chemotherapy at the same site as radiotherapy may experience a reactivation of skin toxicity known as a "recall" phenomenon. Patients who have had previous radiation therapy at the site of injection may develop severe local reactions from extravasated cytotoxic drugs. Cytotoxic drugs also have the potential to cause cutaneous abnormalities in areas that have been damaged previously by radiation, even in areas that are distant from the injection site. Patients who have had an extravasation and receive further chemotherapy in a different site may experience an exacerbation of tissue damage in the original site.

Furthermore, areas of previous surgery where the underlying tissue is likely to be fibrosed and toughened dramatically present an increased risk of extravasation. Radical mastectomy, axillary surgery or lymph node dissection may impair circulation in a particular limb. This reduces venous flow and may allow intravenous solutions to pool and leak around the site of cannulation.

Some chemotherapy drugs often never reach the tumors they are intended to treat because the blood vessels feeding the tumors are abnormal. A tumor's capillaries (small blood vessels that directly deliver oxygen and nutrients to cancer cells) can be irregularly shaped, being excessively thin in some areas and forming thick, snarly clumps in others. These malformations create a turbulent, uneven blood flow, so that too much blood goes to one region of the tumor, and too little to another. In addition, the capillary endothelial cells lining the inner surface of tumor capillaries, normally a smooth, tightly-packed sheet, have gaps between them, causing vessel leakiness.

The systemic and intravenous side effects of chemotherapy coupled with the limited effect of systemic administration due to abnormal characteristics of tumor blood vessels have given the scientific community pause, in searching for more direct, localized and biologic solutions. Accordingly, the oncology literature has become increasingly populated with articles espousing prospective benefits and positive outcomes of intra-tumoral chemotherapy. A direct administration of cytotoxic drugs such as Mytomycin, Mytomycin-C, Bleomycin, Fluorouracil, Mitoxantrone, Cisplatin, and Avastin in endobronchial intra-tumoral chemotherapy has been done experimentally via direct injection of the agent into the endobronchial tumor. In these cases, the tumor was reported to have died and been subsequently removed.

However, while some experimental uses of the localized delivery of cytotoxic drugs have been attempted, there has been little implementation of such drug delivery in practice, possibly due to numerous problems associated with such delivery. First, it is often necessary to deliver cytotoxic drugs to remote and not easily accessible blood vessels and other lumens within body organs, such as lungs. It is also important to be able to deliver defined doses of the cytotoxic substances because such substances are often very expensive or are capable of causing serious harm if delivered in excess. Moreover, the existing methods lack the ability to contain the cytotoxic agent and/or radiation therapy and mitigate collateral damage to non-affected anatomy and structures.

Several devices have been proposed for a targeted delivery of drugs to internal bodily cavities. A solution that has been proposed using a catheter with two balloons to deliver the therapeutic agent, such as those disclosed in U.S. Pat. No. 5,397,307 to Goodwin and U.S. Patent Application No. 2008/0208118 by Goldman. In these systems, first and second balloons are inflated to create a chamber between them, and a therapeutic agent is then introduced into this chamber. While useful for confining the delivery of the agent to a specific target site, these systems are not particularly efficient at infusing the relevant biological material with the drug. Instead, the catheter may need to remain in place for an unnecessarily long period of time while the infusion of the drug into the biological material is allowed to take place. This is undesirable, especially in applications such as pulmonology, where the patient's respiratory passage has been somewhat restricted by the device. Further, this can result in some of the agent never being infused into the targeted material and instead remaining in the cavity and, after the balloon catheter is removed, subsequently migrating to other undesired portions of the body.

What is desired, therefore, is a balloon catheter system for delivering therapeutic and/or diagnostic agents to bodily tissues, tumors, and other biological materials that can locally deliver the agent to a specific target site. What is further desired is a balloon catheter system for delivering therapeutic and/or diagnostic agents that facilitates the extravastion of the drug into surrounding bodily tissues, tumors, and other biological materials. What is also desired is a balloon catheter system for delivering therapeutic and/or diagnostic agents that can adjust for changing conditions during the process of delivering the drug.

SUMMARY OF THE INVENTION

Accordingly, it is an object of the present invention to provide an adjustable balloon catheter system that can deliver therapeutic and/or diagnostic agents to bodily tissues, tumors, and other biological materials from within bodily cavities.

It is a further object of the present invention to provide an adjustable balloon catheter system that can target specific areas for the delivery of therapeutic and/or diagnostic agents to bodily tissues, tumors, and other biological materials.

It is yet another object of the present invention to provide an adjustable balloon catheter system for delivering therapeutic and/or diagnostic agents to bodily tissues, tumors, and other biological materials that can be operated using fluid pressure and/or vacuum.

It is still another object of the present invention to provide an adjustable balloon catheter system for delivering therapeutic and/or diagnostic agents to bodily tissues, tumors, and other biological materials that provide physiological feedback from which the intra-lumen diameter of the bodily cavity can be determined, and the pressure and flow supplied to the balloon can be adjusted accordingly.

It is another object of the present invention to provide an adjustable balloon catheter system for delivering therapeutic and/or diagnostic agents to bodily tissues, tumors, and other biological materials that permits the passage of bodily fluids through the system.

It is still another object of the present invention to provide a resector balloon system for removing undesirable biological material that facilitates exterior imaging.

It is yet another object of the present invention to provide a resector balloon system for removing undesirable biological material that provides visualization from within the bodily cavity.

Other objects of the invention and its particular features and advantages will become more apparent from consideration of the following drawings and accompanying detailed description.

In order to overcome the deficiencies of the prior art and to achieve at least some of the objects and advantages listed, the invention comprises a method of delivery of a therapeutic and/or diagnostic agent to tissue, including inserting a catheter assembly into a bodily cavity, the catheter assembly comprising an outer catheter having a lumen therein and a first balloon, and an inner catheter at least partially disposed in the lumen of the outer catheter and having a second balloon, inflating the first and second balloons by supplying fluid thereto to create a chamber between the first balloon and the second balloon, delivering the therapeutic and/or diagnostic agent to the chamber, and increasing the fluid pressure within the chamber by moving at least one of the first and second balloons toward the other of the first and second balloons.

In certain embodiments, the invention further includes decreasing the fluid pressure within the chamber by moving at least one of the first and second balloons away from the other of the first and second balloons. In some of these embodiments, the invention further includes repeating the steps of increasing the fluid pressure within the chamber and decreasing the fluid pressure within the chamber. In some of those cases, the step of increasing the fluid pressure in the chamber is repeated, the second balloon is closer to the first balloon than the previous time the fluid pressure in the chamber was increased.

In certain embodiments, the step of inflating the first and second balloons comprises supplying fluid to the first and second balloons with an electro-pneumatic pump. In some of these cases, the step of increasing the fluid pressure within the chamber by moving at least one of the first and second balloons comprises determining a diameter within the biological cavity as the moving balloon is moved toward the other of the first and second balloons, and adjusting the amount of inflation of the moving balloon as it is moved toward the other of the first and second balloons based at least in part on the determined diameter.

In certain embodiments, the step of increasing the fluid pressure within the chamber comprises moving the inner catheter through the other catheter to move the second balloon, while in other embodiments, the step of increasing the fluid pressure within the chamber comprises moving the outer catheter over the inner catheter to move the first balloon.

In some embodiments, the step of delivering the therapeutic and/or diagnostic agent comprises delivering the agent to the chamber through at least one opening in the catheter. In other embodiments, the step of delivering the therapeutic and/or diagnostic agent comprises delivering the agent to the chamber through at least one opening in at least one of the first and second balloons by pressing at least one of the first and second balloons against the other of the first and second balloons to urge the therapeutic and/or diagnostic agent into the chamber.

In certain embodiments, the invention further includes providing a vacuum to evacuate at least some of the agent from the chamber. In some cases, the invention further includes using an imaging device disposed in said inner catheter to visualize tissue in the bodily cavity.

In some embodiments, the agent is doxorubicin. In other embodiments, the agent is cisplatin, and the method further includes the step of supplying a second agent, the second agent being epinephrine. In further embodiments, the agent is 5-4 fluorouracil. In yet further embodiments, the agent is a combination of at least one therapeutic agent and at least one biomarker, and the method further includes the step of monitoring extravasation of the at least one therapeutic agent into tissue via the at least one biomarker. In some of these embodiments, the biomarker is a radio-opaque marker.

The invention also includes method of delivery of a therapeutic and/or diagnostic agent to tissue, including inserting a catheter comprising a first balloon into a bodily cavity, inflating the first balloon by supplying fluid thereto, inserting a second balloon into the bodily cavity by passing the second balloon through a lumen in the catheter until the second balloon is positioned distally of the first balloon, inflating the second balloon by supplying fluid thereto to create a chamber between the first balloon and the second balloon, delivering the therapeutic and/or diagnostic agent to the chamber, and increasing the fluid pressure within the chamber by moving at least one of the first and second balloons toward the other of the first and second balloons.

The invention also includes an adjustable balloon catheter system for delivering a therapeutic and/or diagnostic agent to tissue, including an outer catheter having a first lumen therein and a first balloon, an inner catheter at least partially disposed in the first lumen and having a second balloon, wherein the outer catheter has a first balloon supply lumen through which fluid is supplied to said first balloon to inflate the first balloon, and the inner catheter has a second balloon supply lumen through which fluid is supplied to the second balloon to inflate the second balloon and create a chamber between the first and second balloons, wherein at least one of the inner and outer catheters has an agent lumen therein for delivering a therapeutic and/or diagnostic agent to the chamber, and wherein the inner catheter is movably disposed in the first lumen such that the inner catheter moves relative to the outer catheter.

In some embodiments, the inner catheter has the agent lumen, the inner catheter having at least one opening therein through which the therapeutic and/or diagnostic agent enters the chamber from the agent lumen. In other embodiments, the outer catheter has the agent lumen, the outer catheter having at least one opening therein through which the therapeutic and/or diagnostic agent enters the chamber from the agent lumen.

In certain embodiments, the inner catheter has the agent lumen, the agent lumen is in fluid communication with the second balloon, and the second balloon has at least one opening therein through which the therapeutic and/or diagnostic agent enters the chamber from the second balloon. In other embodiments, the outer catheter has the agent lumen, the agent lumen is in fluid communication with the first balloon, and the first balloon has at least one opening therein through which the therapeutic and/or diagnostic agent enters the chamber from the first balloon.

In some cases, the inner catheter further includes a piston movably disposed in the first lumen, and an additional lumen having an opening into the first lumen through which at least one of a fluid and a vacuum is provided to the first lumen to move the piston within the first lumen such that the second balloon moves relative to the first balloon. In other cases, the inner catheter includes a piston movably disposed in the first lumen, and the outer catheter includes an additional lumen having an opening into the first lumen through which at least one of a fluid and a vacuum is provided to the first lumen to move the piston within the first lumen such that the second balloon moves relative to the first balloon.

In some embodiments, the invention includes a fluid source that provides fluid to the first balloon supply lumen and the second balloon supply lumen. In some cases, the fluid source comprises an electro-pneumatic pump. In certain cases, the fluid source includes at least one sensor for making at least one measurement, and a processor that determines a diameter of a biological cavity based at least partially on the at least one measurement, wherein the fluid source adjusts the amount of fluid supplied to the second balloon based at least in part on the determined diameter. In some embodiments, the fluid is a gas.

In certain embodiments, the invention further includes at least one imaging marker mounted adjacent the second balloon. In some of these embodiments, the at least one imaging marker comprises a radio-opaque ring. In some embodiments, the inner catheter includes a distal tip with an opening therein and an additional lumen in fluid communication with the opening in the distal tip for passing bodily fluids therethrough.

In certain embodiments, the system further includes an imaging device disposed in at least one of the inner and outer catheters.

In some embodiments, the system includes a pharmacological agent that passes through the agent lumen.

In certain embodiments, the system includes a contrast agent that passes through the agent lumen.

BRIEF DESCRIPTION OF THE DRAWINGS

FIG. 2A is a partially exposed, isometric view of the catheter assembly of FIG. 1 positioned in a bodily cavity.

FIG. 2B is a cross-sectional view of the catheter assembly of FIG. 2A.

FIG. 2C is a cross-sectional view of another embodiment of the catheter assembly of FIG. 2A.

DETAILED DESCRIPTION OF THE INVENTION

Figure 1:
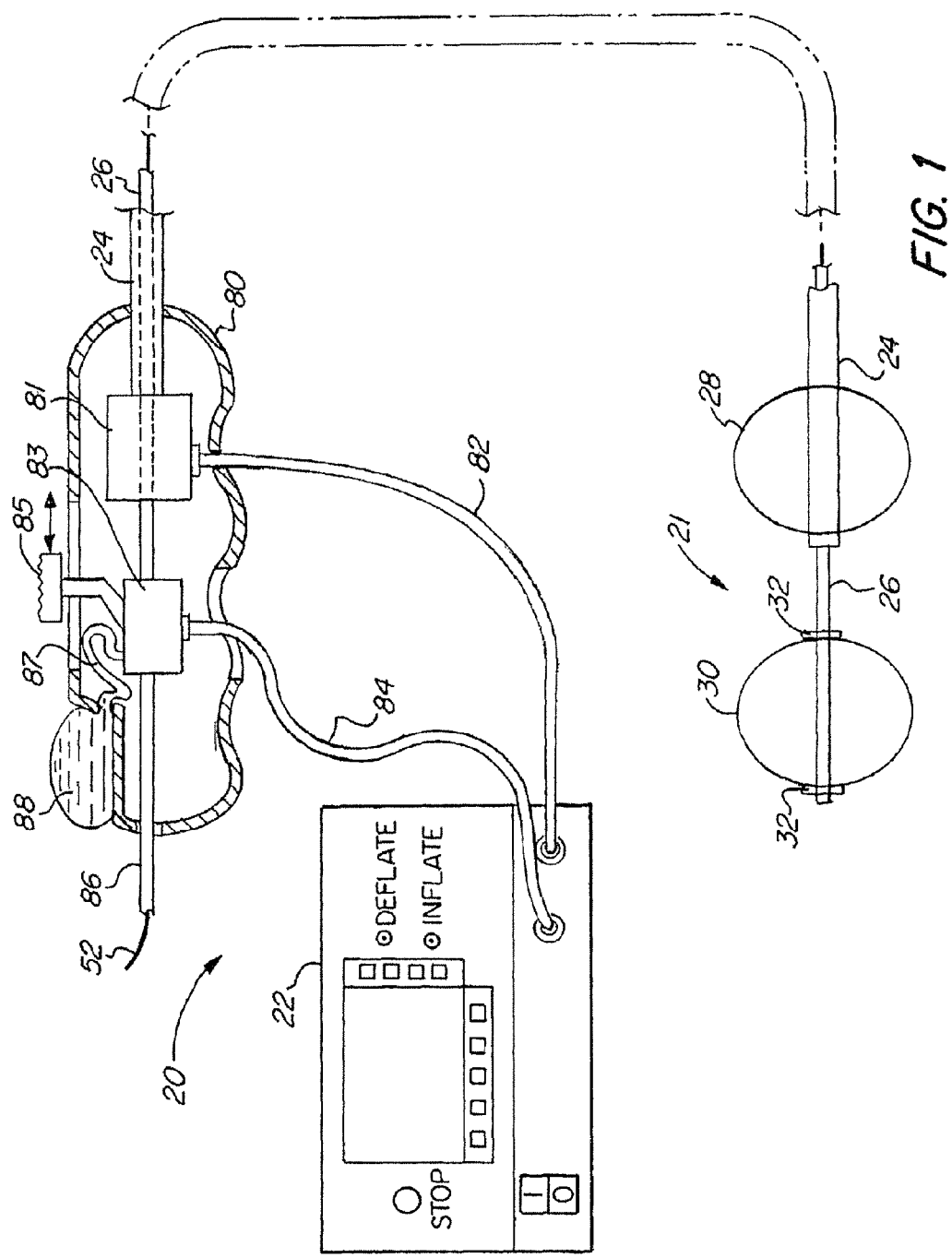
FIG. 1 is a schematic view of a balloon catheter system for delivering therapeutic and/or diagnostic agents in accordance with the invention.

The basic components of one embodiment of an adjustable balloon catheter in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1, the adjustable balloon catheter system (20) includes a catheter assembly (21) and a fluid source (22), such as an electro-pneumatic pump having controls on the front thereof, from which a physician or assistant can control the system (as well as a remote control unit), such as that disclosed in U.S. Patent Application No. 2010/0121270 by Gunday et al., the specification of which is hereby incorporated by reference herein in its entirety. The pump (22) is connected to the catheter assembly (21), to which the pump (22) supplies a fluid, such as a gas, liquid, or mixture thereof. The pump (22) includes a variety of capabilities for balloon identification, proper inflation/deflation of the balloons, and feedback measurements, many details of which are described in Gunday et al. The catheter assembly (21) includes an outer catheter (24) with a first balloon (28), and an inner catheter (26) with a second balloon (30). The catheters (24, 26) may have any suitable diameter and length depending on a particular application, and may be flexible, rigid, or semi-rigid. The catheters (24, 26) may be made with any commercially available material that is flexible enough to allow them to be safely inserted through the available opening of a bodily cavity such that it will bend and not puncture the walls of that bodily cavity, yet at the same time, is rigid enough that it will maintain its shape as it is passed alongside and/or through the available opening of the bodily cavity.

The balloons (28, 30) may be made of latex or other suitable material, and may come in a variety of sizes and diameters, which allow the adjustable balloon catheter to be used in bodily cavities of various diameters and dimensions, such as large and small bronchial branches, sinuses, and blood vessels, having different types of tumors and tissues to be treated. The pump (22) supplies the air at a pressure of approximately 2 atmospheres in order to be able to inflate such balloons to full size, ranging from 2.5 mml to 50 mml.

In certain advantageous embodiments, at least one of the balloons (28, 30) includes imaging markers (32), such as radio opaque rings, located at or near the ends thereof. Such markers can be selected and appropriately positioned in order to reflect the relevant waves of various imaging modalities (e.g., x-ray) in order to allow the use of such modalities to assist with the precise positioning of the balloons (28, 30).

Referring to FIGS. 2A-B, outer catheter (24) has a main lumen (34) therein. The inner catheter (26) is movably disposed in the lumen (34), such that the inner catheter (26) can slide within the outer catheter (24). The outer catheter (24) has another lumen (36) with an opening (38), through which fluid is supplied by the aforementioned fluid source (22) to the first balloon (28) to inflate the balloon. Likewise, the inner catheter (26) has a lumen (40) therein with an opening (42), through which fluid is supplied by the fluid source (22) to the second balloon (30) to inflate the balloon.

At least one of the outer and inner catheters (24, 26) has a lumen with an opening for delivering a therapeutic and/or diagnostic agent. For example, in some embodiments, the inner catheter (26) has a lumen (44) that leads to an opening (54) for delivering such an agent. Likewise, in some embodiments, the outer catheter (24) has a lumen (45) that leads to an opening (55) for delivering a therapeutic and/or diagnostic agent. In some cases, both the outer and inner catheters (24, 26) have lumens and openings for delivering agents in this way.

Similarly, multiple lumens may be provided in a single catheter for the delivery of multiple agents. For example, the inner catheter (26) may have a number of lumens therein, including the lumen (40) for communicating air to the opening (42) and into the second balloon (30) for inflation, the lumen (44) leading to the opening (54) for a first therapeutic or diagnostic agent, as well as another lumen (46) leading to an opening (56) for a second therapeutic or diagnostic agent. The inner catheter (26) may also include a lumen (48) for delivering air or another fluid to an actuation mechanism (as further described below), or for accommodating an imaging device and/or illumination system for assisting with the placement of the balloon (30) within the bodily cavity (as further described below), as well as a central lumen (50) that acts as a bypass lumen for bodily fluids, such as air or blood, and/or for accommodating a guide wire to further facilitate insertion of the catheter assembly.

Any of various arrangements for the various lumens for the delivery of therapeutic/diagnostic agents, or fluid for operation activation mechanisms, is possible. For example, as shown in FIG. 2C, the inner catheter (26) may have an air bypass lumen (150) bored through its center, as well as a balloon air lumen (140) and a first therapeutic agent lumen (144) bored therethrough at other positions along its periphery. Meanwhile, the outer catheter (24) may have a balloon air lumen bored therethrough, as well as a second therapeutic agent lumen (146) and an actuation air lumen (148).

By employing multiple lumens to supply therapeutic agents in this fashion, one can deliver multiple agents separately, as may be desired, for example, when using two different pharmaceuticals that should not be mixed until just before being extravasated into bodily tissue. Likewise, one may need to deliver one medicinal agent at the beginning of the procedure, and another medicinal agent at a later time during the procedure, without contaminating the later agent with traces of the first one that may remain in the lumen used to deliver the first agent. Indeed, one may even wish to deliver a second agent at a slightly different location than the first agent, which can be accomplished by repositioning the catheter assembly (21), as further described below.

Figure 3A:
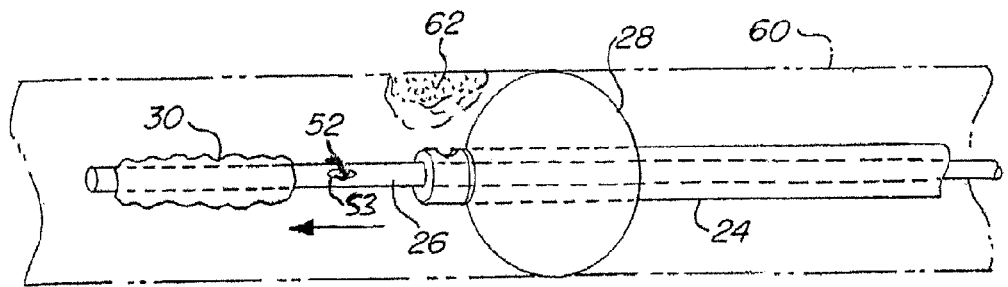
FIG. 3A is a partially exposed, isometric view of the catheter assembly of FIG. 2A being positioned in a bodily cavity at a target site.

The operation of the adjustable balloon catheter system (20) is illustrated stepwise in FIGS. 3A-D. The assembly is first inserted into a bodily cavity (60) until the balloon (28) is in the vicinity of the target site, which in this case, is a tumor (62). As shown in FIG. 3A, once the outer catheter (24) reaches the desired position along the bodily cavity (60), the proximal balloon 38 is inflated in order to anchor the assembly in place. The inner catheter (26), which slides within the aforementioned lumen (34) as described above, is pushed axially through the outer catheter (24) until the distal balloon (30) is also positioned in the desired location.

In some cases, an imaging device (52), which can be pushed through a lumen (48) and out through a hole (53), can be used to help position the balloon (30) at the proper location. Alternatively, the lumen (44) that delivers the therapeutic and/or diagnostic agent may be large enough to also accommodate the imaging device (52), such that the device (52) can exit the same opening (54) as the agent. In some embodiments, one or both of the balloons (28, 30) is transparent, and the imaging device (52) can be pushed through one the lumens (36, 40) through which fluid is supplied to the balloons for inflation thereof, and out the corresponding opening (38, 42) and into one of the transparent balloons (28, 30) in order to view the surrounding area.

The imaging device (52) can be any device suitable for viewing the target area, such as a coherent fiber bundle or appropriate optical element and lens assembly in conjunction with an imaging sensor (e.g., CMOS, CCD), having a sufficiently small outer diameters, such as, for example, 0.75 mm-1.2 mm. In some cases, the imaging device (52) has a pre-shaped distal tip that enables it to easily extend through one of the aforementioned openings.

In some embodiments, the inner catheter (26) is already disposed in the outer catheter (24), such that the distal tip of the inner catheter (26) and the balloon (30) are already located distally of the balloon (28), at the time the catheter assembly (21) is inserted into the bodily cavity (60). However, it should be noted that, in some embodiments, only the outer catheter (24) and balloon (28) are initially inserted into the bodily cavity (60). In these embodiments, the distal tip of the inner catheter (26) and the balloon (30) are inserted into the lumen (34) of the outer catheter (24) at the proximal end of the outer catheter (24), for instance, via a touhy borst type adaptor, and the inner catheter (26) and balloon (30) are then pushed through the lumen (34) until they exit the distal end of the outer catheter (24).

Figure 3B:
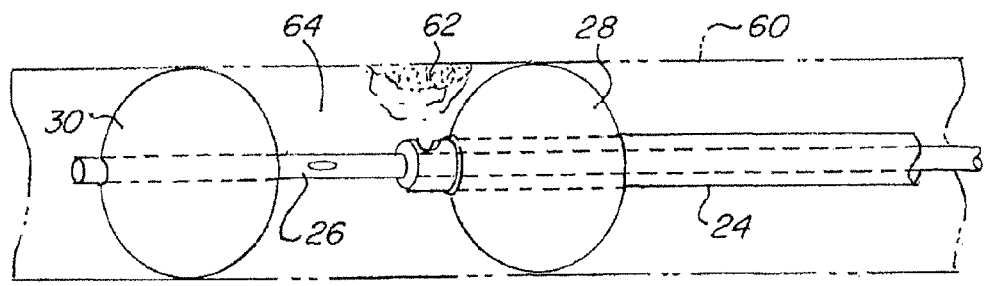
FIG. 3B is a partially exposed, isometric view of the catheter assembly of FIG. 3A when the distal balloon is inflated.
Figure 3C:
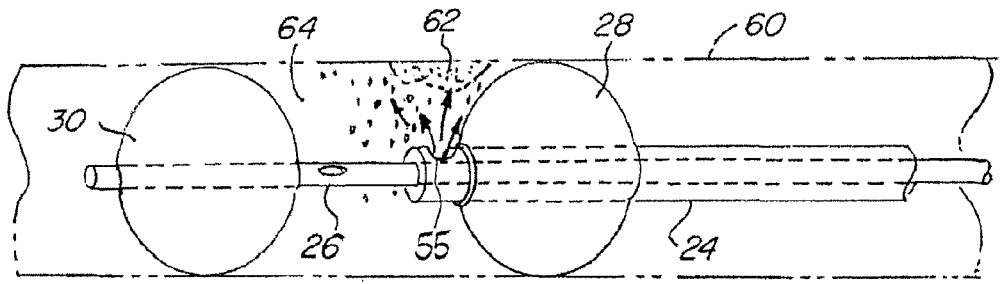
FIG. 3C is a partially exposed, isometric view of the catheter assembly of FIG. 3B when a therapeutic agent is delivered to the target site.

As shown in FIG. 3B, once positioned at the proper location, the distal balloon (30) is inflated to create a chamber (64) between the balloons (28, 30). Referring to FIG. 3C, a therapeutic agent is then supplied through the aforementioned drug delivery lumen (45) and delivered into the chamber (64) via the opening (55).

Figure 3D:
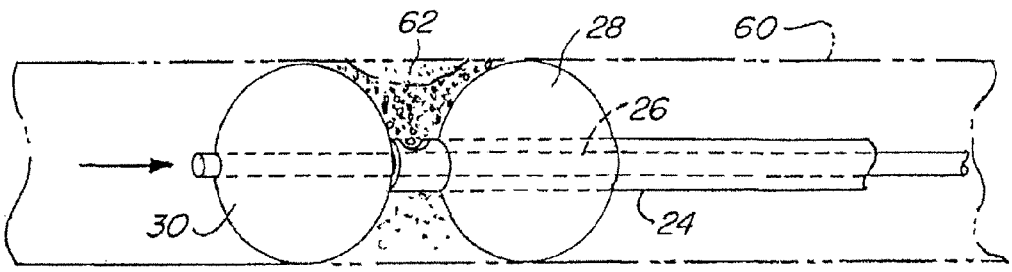
FIG. 3D is a partially exposed, isometric view of the catheter assembly of FIG. 3C when the distal balloon is moved closer to the proximal balloon to facilitate extravasation of the therapeutic agent.

As shown in FIG. 3D, the distal balloon 30 is then moved towards the proximal balloon (28) by pulling the inner catheter (26) back through the lumen (34) of the outer catheter (24). In doing so, the volumetric pressure in the chamber (64) is increased, such that it facilitates extravasation of the therapeutic agent into the surrounding tissue. This application of volumetric pressure to the surface of the airway or the vessel wall neutralizes hemodynamic shear forces and helps facilitate the cellular absorption of the diagnostic and/or therapeutic agents. If necessary, the inner catheter (26) can be repeatedly pushed and pulled through the outer catheter (24) in this way for a certain amount of time such that the target tissue is washed under pressure with a drug.

In some embodiments, the pump (22) has at least one sensor for making a measurement (e.g., pressure), and a processor that determines a diameter of the biological cavity based on that measurement. Based on this the determination, the pump (22) can adjust the amount of fluid supplied to the second balloon (30) to accommodate changes in the diameter of the bodily cavity at different locations as the balloon (30) is moved through the cavity, or which may simply result with the passage of time during a procedure.

Any of various agents useful in therapeutic application can be delivered in the above described manner. For example, the agent may comprise one or more chemical or biological drugs with useful pharmacological properties, as well as any other medicaments or other substances with medicinal or other therapeutic uses. Such agents may be synthetic or natural, so long as they have an advantageous therapeutic effect that can obtained by delivering the agent to a target site. In certain embodiments, agents particularly useful for chemotherapies, radiation therapies, or immunotherapies are delivered as described above.

In some advantageous embodiments, a cytotoxic substance or other agent useful for chemotherapy is delivered to a target site via one or more of the aforementioned lumens. For example, in some cases, the catheter assembly is used to deliver a chemical agent that affects cell division or DNA synthesis. Such agents include, for example, alkylating agents, such as cisplatin, carboplatin, oxaliplatin, mechlorethamine, BCNU (carmustine), cyclophosphamide, chlorambucil, ifosfamide, busulfan, treosulfan, melphelan/melphalan hydrochloride, thiotepa, dacarbazine, procarbazine, streptozotocin, CCNU (lomustine), and semustine; anti-metabolites, such as azathioprine, mercaptopurine, thioguanine, fludarabine, pentostatin, 2-CDA (cladribine), fluorouracil, floxuridine, cytosine arabinoside (cytarabine), gemcitabine/gemcitabine hydrochloride, methotrexate, pemetrexed, and tomudex; anthracenedione agents, such as mitoxantrone; anthracyclines, such dactinomycin, daunorubicin, doxorubicin, epirubicin, idarubicin, valrubicin, aclarubicin, and bleomycin; plant alkaloids and terpenoids, such as noscapine, vincristine/vincristine sulfate, vinblastine/vinblastine sulfate, vinorelbine/vinorelbine tartrate, vindesine, podophyllotoxin, paclitaxel, and docetaxel; topoisomerase inhibitors, such as irinotecan, topotecan/topotecan hydrochloride, amsacrine, etoposide, etoposide phosphate, and teniposide; and other agents with similar mechanisms of action, such as mitomycin C.

Other such agents include those that target molecular abnormalities, including tyrosine kinase inhibitors, such as crizotinib, gefitinib, erlotinib hydrochloride, imatinib, and imatinib mesilate. Still other such agents include those that modulate tumor cell behavior without actually attacking the cells, such as may be employed for hormone treatments. Indeed, any antineoplastic drug known to efficacious in treating cancerous cells, such as hydroxyurea or diltiazem augment taxol, may be employed.

In certain advantageous embodiments, a biological response modifier or other biological agent useful for immunotherapy is delivered to a target site via one or more of the aforementioned lumens. Such agents, which are often cytokines, may be a recombinant, synthetic, or natural preparation. These biological agents may include, for example, interferons, such as alpha-interferons and beta-interferons; interleukins, such as aldesleukin; colony-stimulating factors, such as filgrastim, sargramostim, epoetin, and oprelvekin; monoclonal antibodies, such as herceptin, rituxan, edrecolomab, gemtuzumab, alemtuzumab, nimotuzumab, cetuximab, bevacizumab, ibritumomab, panitumumab, and tositumomab; cancer vaccines; gene therapies; non-specific immunomodulating agents; and angiogenesis inhibitors. Any biologic known to useful for immunotherapies, such as asparaginase, may be employed.

In some advantageous embodiments, the therapeutic agent is delivered in drug eluting microspheres, which can be used both to cause the embolization of blood vessels that supply undesirable tissues and to retain the drug in a localized area for a sustained period of time. For example, drug-eluting microspheres can be used to deliver a chemotherapeutic drug, such as doxorubicin, to a tumor. When the microspheres reach the target site, they will block vessels supplying the tumor, and this suppression of blood flow will lead to ischemia. Over time, the microspheres break down, and the drug will be absorbed by the tissue. As a result, not only is a localized sustained realease of the drug achieved, but the ischemia will also increase the effect of the drug on the tumor.

The above described delivery of therapeutic agents is also useful for radiation therapies, in which high-energy radiation is used to kill cancer cells and shrink tumors. One method of such therapy places radioactive material in the body near the cancer cells. Thus, in certain advantageous embodiments, a radioactive substance, such as a radio labeled monoclonal antibody, is supplied via one of various lumens and extravasated into nearby tissue as described above.

Various agents may also be employed to assist in making diagnostic observations or monitoring procedures. For example, in some advantageous embodiments, the above described system may be used to deliver a contrast agent that allows or improves visualization via one or imaging modalities, which can be used to image the extravasation of the agent into the surrounding tissues throughout the course of a procedure. Such agents may include, for example, radio contrast agents, such as iodine or barium, to improve X-ray based imaging techniques; MRI contrast agents, such as gadolinium, to improve magnetic resonance imaging; and microbubble contrast agents, to improve ultrasound imaging.

In some advantageous embodiments, biomarkers are used together with a therapeutic agent to observe and monitor the extravasation of the agent into the surrounding tissues. In some of these advantageous embodiments, CF3PM & MTFN-1 fluorinated radio-opaque biomarkers are used. The biomarkers may be detected by various non-invasive imaging modalities, such as X-Ray, MRI, CT, ultrasound, spectroscopy, etc.

With the addition of an appropriate inert dye or contrast media (e.g., radioactive, polarized, florescent, temperature sensitive) to a drug to be extravasated, the drug infusion rate and the amount of drug infused into the tissue can be monitored, quantified, and recorded/displayed, such as, for example, by capturing and storing sequential video frames under different illumination conditions (UV, IR, polarized, color filters, etc.). Further, by deploying a contrast agent along with a therapeutic agent, one can visually identify the extravasation depths and/or discern the requisite volumetric pressure, force, temperature, frequency and/or time to achieve efficacious delivery of the therapeutic agent to the desired depth of penetration at the intended treatment site.

In some embodiments, a third balloon is located distally of balloon (30), and can be inflated to both assist anchoring the assembly in place within the bodily cavity and to create a chamber between this third balloon and the inflated balloon (28). In this way, even if the balloon (30) is partially deflated when it is moved through the bodily cavity, the therapeutic and/or diagnostic agent will still be retained in the vicinity of the target site.

Once the agents have been delivered and extravasted into the tissue at the target site any remaining agent can be evacuated from the chamber (64) via the same openings and lumens through which they were supplied to the chamber (64) using suction. In certain advantageous embodiments, the fluid source (22) produces a negative atmospheric pressure to vacuum out the agents. Alternatively, additional lumens and corresponding openings may be employed in the manner previously described to evacuate the agents through lumens different from those used to supply the agents to the chamber (64). Regardless, the various lumens and corresponding openings can be used to cyclically deliver and evacuate the agents and various other fluids instantly, sequentially, intermittently and/or continuously over designated time intervals.

In some embodiments, one of the lumens of the outer or inner catheters (24, 26) is used to supply an irrigation fluid. For example, when using both a therapeutic agent and a contrast agent, once the contrast agent has reached, and sufficiently saturated, the intended treatment site, any remaining contrast agent can be vacuumed out of the chamber (64). The chamber (64) can then be irrigated, lavaged, and suctioned to remove any residual agent.

In addition to adjusting the fluid pressure in the chamber (64) by repeatedly pushing and pulling the inner catheter (26) through the outer catheter (24), an elevated pressure within the chamber (64) can be maintained, or further increased, by supplying additional fluid into the chamber (64) via one of the aforementioned lumens having an opening into the chamber (64). In some embodiments, inline pressure valves that enable the lumens to be pressurized, while preventing unintended de-pressurization, are provided. In certain embodiments, one or more pressure transducers are used to measure the pressure in the lumens in order to safely regulate the delivery rate of the agent and detect any problems that may arise.

In some embodiments, the inner catheter (26) is manually moved relative to the outer catheter (24) using, for example, a handheld device such as that further described below. However, it should be noted that the inner catheter (26) can alternatively be moved using a motor.

The motion of the inner catheter (26) through the lumen (34) of the outer catheter (24) can normally be achieved by manually sliding the inner catheter (24) back and forth from the proximal end of the catheter system. Additionally, the system (20) includes some kind of breakout junction or adaptor assembly sufficient to facilitate the introduction of inflation fluids, air bypass, therapeutic/diagnostic agents, and/or other devices, such as an imaging device, through the catheters.

One example of such an assembly is illustrated in FIG. 1. A hand piece (80) houses the assembly, which includes an adaptor (81), such as a touhy borst adaptor, connected to the outer catheter (24) and supplied with air from the pump (22) via a supply line (82). Another adaptor (83) is connected to the inner catheter (26) and supplied with air from the pump (22) via a supply line (84). The inner catheter (26) extends through a sealed valve of the adaptor (81), through the adaptor (81), and into the lumen (34) of the outer catheter (24). A knob (85) on the hand piece (80) is connected to the adaptor (83), such that a user can move the adaptor (83) back and forth within the hand piece (80) by sliding the knob (85), thereby also moving the inner catheter (26) connected thereto.

Another section (86), which may be part of the adaptor (83) or a separate piece inserted into the back of the adaptor (83), extends out of the back of the hand piece (80). This allows one or more lumens of the inner catheter (26), such as another fluid/device lumen (48) and/or central air bypass lumen (50) to be extended all the way through the hand piece (80).

The adaptor (83) is also supplied with at least one therapeutic and/or diagnostic agent via a supply line (87) connected thereto. This agent may be provided from any of various sources, such as, for example, a drug capsule (88) mounted to or inserted into the hand piece (80). The interior of the adaptor (83) is appropriately compartmentalized such that the agents and or fluids are directed into only the proper lumen(s).

Figure 4A:
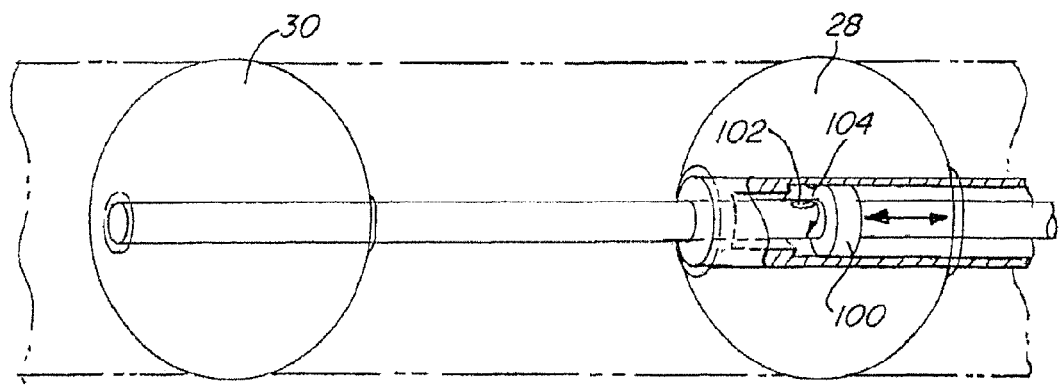
FIG. 4A is a partially exposed, isometric view of the catheter assembly of FIG. 2A employing a fluid-driven piston to move the inner catheter of the assembly.

It should be noted that, while the particular hand piece (80) and assembly therein has been described, any suitable mechanism for moving the inner catheter (26) relative to the outer catheter (24), and for introducing one or more agents, fluids and/or devices into the outer/inner catheters (24, 26), may be employed. Though the movement of the inner catheter (26) relative to the outer catheter (24) has been described above as effected either manually or by motor, in some embodiments, a fluid, which may be supplied by the fluid source (22), can be used for this purpose. For example, as illustrated in FIG. 4A, a portion of the lumen (34) of the outer catheter (24) may have an diameter that is slightly larger than the outer diameter of the inner catheter (26) to create a channel (104) in which a piston (100) slides. Fluid, such as air, is supplied by the fluid source (22) to a lumen of the inner catheter (26), such as lumen (48), and out through an opening (102) into the channel (104), which moves the piston (in the illustration of FIG. 4A, to the right). The fluid source (22) can likewise supply a vacuum via the lumen and opening (102) in order to move the piston (100) in the opposite direction (in the illustration of FIG. 4A, to the left).

Figure 4B:
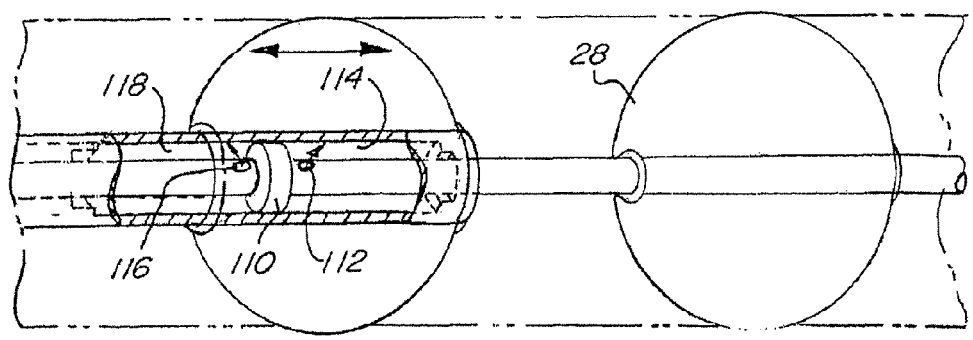
FIG. 4B is a partially exposed, isometric view of the catheter assembly of FIG. 2A employing a fluid-driven piston to move the outer catheter of the assembly.
Figure 5A:
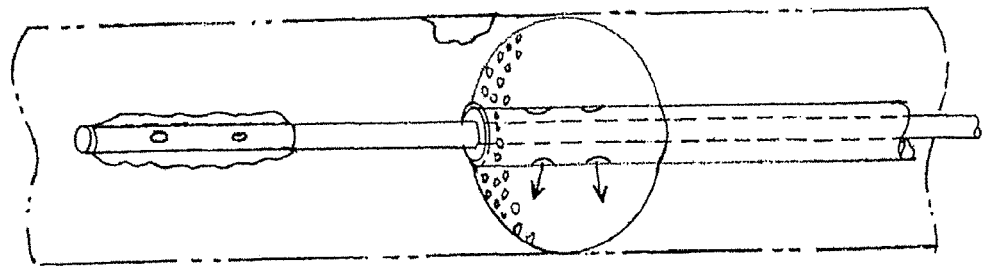
FIG. 5A is a partially exposed, isometric view of another embodiment of the catheter assembly of FIG. 1.
Figure 5B:
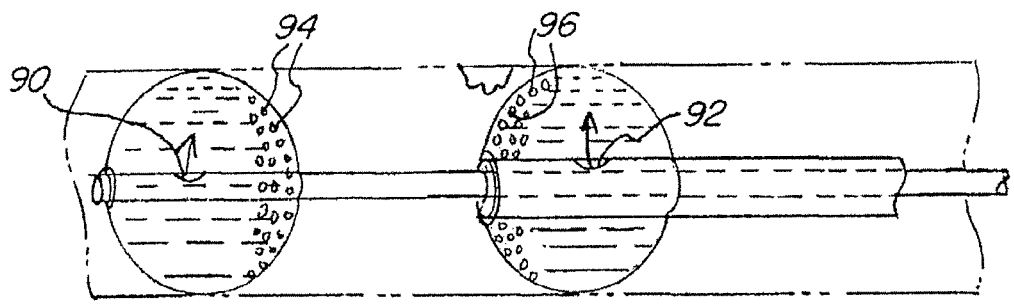
FIG. 5B is a partially exposed, isometric view of the catheter assembly of FIG. 5A when the distal balloon is inflated.
Figure 5C:
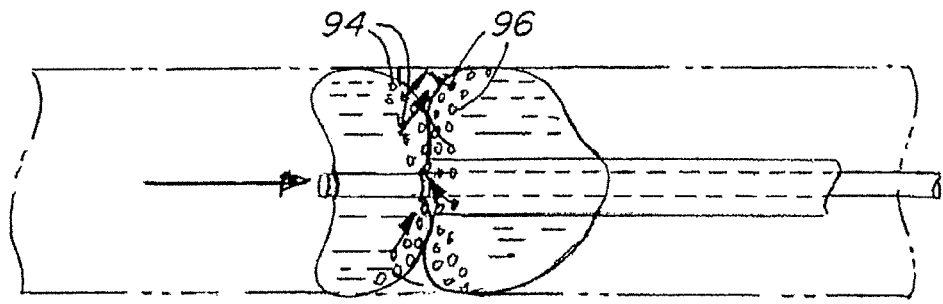
FIG. 5C is a partially exposed, isometric view of the catheter assembly of FIG. 5B when the distal balloon is moved closer to the proximal balloon to facilitate the supply and extravasation of a therapeutic agent.

It should be noted that, though the balloon moved by the inner catheter (26) has generally been depicted as the distal balloon (30), in some embodiments, it is the proximal balloon (28) that is moved in this way, as shown in FIG. 4B. In these cases, the catheter assembly (21) is inserted into the bodily cavity, and the distal balloon (30) is first inflated into order to anchor the assembly in place. The proximal balloon (28) is then moved to the desired location by sliding the inner catheter (26) relative to the outer catheter (24). As noted above, this can be done by manually moving the inner catheter (26) by the user at a proximal location outside the body. Indeed, in some cases, both the proximal and distal balloons (28, 30) are moved by pulling and/or pushing both the outer and inner catheters (24, 26) to move the balloons relative to each other.

However, as shown in FIG. 4B, a fluid and piston arrangement can be employed. Fluid, such as air, is supplied by the fluid source (22) to a lumen of the inner catheter (26), such as lumen (48), and out through an opening (112) into the channel (114), which moves the piston (in the illustration of FIG. 4B, to the left). The fluid source (22) can likewise supply a vacuum via the lumen and opening (112) in order to move the piston (110) in the opposite direction (in the illustration of FIG. 4B, to the right).

In embodiments described in FIGS. 4A-B, two lumens can be employed to separately supply fluid to two openings on either side of the piston. For example, as illustrated in FIG. 4B, a second opening (116) is shown on the opposite side of the piston (110), through which fluid can be supplied to a channel (118). In this way, the piston (110) can be moved back and forth simply by alternately supplying and releasing air on either side of the piston (110) via openings (112, 116).

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of delivery of a therapeutic and/or diagnostic agent to tissue, the method comprising:
    inserting a catheter assembly into a bodily cavity, the catheter assembly comprising
        an outer catheter having a lumen therein, an outer wall, and a first balloon, and
        an inner catheter at least partially disposed in the lumen of the outer catheter, the inner catheter having an outer wall and and a second balloon;
    inflating the first and second balloons by supplying fluid thereto to create a chamber between the first balloon and the second balloon, said chamber having a volume;
    delivering the therapeutic and/or diagnostic agent through at least one opening in at least one of the outer walls of the inner and outer catheters positioned between the first and second balloons to the chamber between the first and second balloons; and
    increasing the fluid pressure within the chamber containing the therapeutic and/or diagnostic agent by moving at least one of the first and second balloons toward the other of the first and second balloons to decrease the volume of the chamber.

2. The method of claim 1, further comprising the step of decreasing the fluid pressure within the chamber by moving at least one of the first and second balloons away from the other of the first and second balloons.

3. The method of claim 2, further comprising repeating the steps of increasing the fluid pressure within the chamber and decreasing the fluid pressure within the chamber.

4. The method of claim 3, wherein, when the step of increasing the fluid pressure in the chamber is repeated, the second balloon is closer to the first balloon than the previous time the fluid pressure in the chamber was increased.

5. The method of claim 1, wherein the step of inflating the first and second balloons comprises supplying fluid to the first and second balloons with a electro-pneumatic pump.

6. The method of claim 5, wherein the step of increasing the fluid pressure within the chamber by moving at least one of the first and second balloons comprises:
    determining a diameter within the biological cavity as the moving balloon is moved toward the other of the first and second balloons; and
    adjusting the amount of inflation of the moving balloon as it is moved toward the other of the first and second balloons based at least in part on the determined diameter.

7. The method of claim 1, wherein the step of increasing the fluid pressure within the chamber comprises moving the inner catheter through the other catheter to move the second balloon.

8. The method of claim 1, wherein the step of increasing the fluid pressure within the chamber comprises moving the outer catheter over the inner catheter to move the first balloon.

9. The method of claim 1, wherein the step of delivering the therapeutic and/or diagnostic agent further comprises delivering the agent to the chamber through at least one opening in at least one of the first and second balloons by pressing at least one of the first and second balloons against the other of the first and second balloons to urge the therapeutic and/or diagnostic agent into the chamber.

10. The method of claim 1, further comprising providing a vacuum to evacuate at least some of the agent from the chamber.

11. The method of claim 1, further comprising the step of using an imaging device disposed in said inner catheter to visualize tissue in the bodily cavity.

12. The method of claim 1, wherein the agent is doxorubicin.

13. The method of claim 1, wherein the agent is cisplatin, and wherein the method further comprises the step of supplying a second agent, said second agent being epinephrine.

14. The method of claim 1, wherein the agent is 5-4 fluorouracil.

15. The method of claim 1, wherein the agent is a combination of at least one therapeutic agent and at least one biomarker, and wherein the method further comprises the step of monitoring extravasation of the at least one therapeutic agent into tissue via the at least one biomarker.

16. The method of claim 15, wherein the biomarker is a radio-opaque marker.

* * * * *